(12) United States Patent
Sivakumar et al.

(10) Patent No.: US 9,898,817 B2
(45) Date of Patent: Feb. 20, 2018

(54) SOFTWARE TOOL FOR BREAST CANCER SCREENING

(71) Applicant: Niramai Health Analytix Pvt Ltd, Bangalore (IN)

(72) Inventors: Gayatri Sivakumar, Kerala (IN); Shubhi Sharma, Karnataka (IN); Himanshu J. Madhu, Maharashtra (IN); Arun Koushik Parthasarathy, Mysore (IN); Krithika Venkataramani, Bangalore (IN); Siva Teja Kakileti, Andhra Pradesh (IN)

( * ) Notice: Subject to any disclaimer, the term of this patent is extended or adjusted under 35 U.S.C. 154(b) by 24 days.

(21) Appl. No.: 15/053,767

(22) Filed: Feb. 25, 2016

(65) Prior Publication Data
US 2017/0249738 A1    Aug. 31, 2017

(51) Int. Cl.
*G06K 9/00* (2006.01)
*G06T 7/00* (2017.01)
*G06F 19/00* (2018.01)

(52) U.S. Cl.
CPC .......... *G06T 7/0014* (2013.01); *G06F 19/321* (2013.01); *G06F 19/345* (2013.01); *G06T 2207/10048* (2013.01); *G06T 2207/20092* (2013.01); *G06T 2207/30068* (2013.01); *G06T 2207/30096* (2013.01)

(58) Field of Classification Search
CPC .................... G06T 7/0014; G06T 2207/20092
See application file for complete search history.

(56) References Cited

U.S. PATENT DOCUMENTS

| | | | | |
|---|---|---|---|---|
| 7,298,877 B1 * | 11/2007 | Collins | ................... | G01N 23/04 378/1 |
| 8,300,908 B2 * | 10/2012 | Schneider | ............. | G06T 7/0012 382/128 |
| 9,317,761 B2 * | 4/2016 | Kong | ................... | G06K 9/00885 |
| 2003/0081822 A1 * | 5/2003 | Takeo | ................... | G06T 7/0012 382/132 |
| 2007/0183641 A1 * | 8/2007 | Peters | ................... | G06T 7/0012 382/131 |
| 2011/0215930 A1 * | 9/2011 | Lee | .......................... | G06K 9/00 340/573.1 |
| 2017/0098310 A1 * | 4/2017 | Chefd'hotel | .............. | G06T 7/12 |

* cited by examiner

*Primary Examiner* — Oneal R Mistry
(74) *Attorney, Agent, or Firm* — The Law Office of Austin Bonderer, PC; D. Austin Bonderer

(57) ABSTRACT

What is disclosed is a software tool which enables medical practitioners to manually or automatically analyze a thermal image of an area of breast tissue for the presence of tumorous tissue. In one embodiment, the software interface tool disclosed herein comprises a patient details object which enables the display of a patient details screen wherein a user can enter/edit patient information. A thermal analysis object enables a user to analyze a displayed thermal image of a breast of a patient for breast cancer screening and to classify tissue identified in the thermal image as being tumorous. A modalities object concludes the patient evaluation, persists all data collected from other sections of the tool, and generates reports for documentation purposes. The information can be captured from a database and edited and analyzed further using the tool. Also, report containing all the relevant data is generated for doctor's reference.

19 Claims, 4 Drawing Sheets

SOFTWARE TOOL FOR BREAST CANCER SCREENING

TECHNICAL FIELD

The present invention is specifically directed to a software tool which enables medical practitioners to manually or automatically classify tissue identified in a thermal image of a patient's breast as being tumorous tissue.

BACKGROUND

Breast cancer incidence rates are relatively high in women. Nearly 1 in 8 women in the western world and nearly 1 in 11 women in India will have breast cancer. In the western world, it is the leading cancer in women. In India, for example, it is the second after cervical cancer. Early detection is key to survival as the mortality rates are high for advanced stages. Thermography is an emerging alternative non-invasive and non-contact screening method for breast cancer detection. Thermal imaging captures the infra-red emissivity from the human body in the 7-10 μm wavelength range. Thermal imaging devices are useful for the detection of thermal activity in breast tissue due to a tumor's growth being enabled by causing new blood vessels to grow disproportionately through angiogenesis in the area of the tumor relative to surrounding tissue. This increased biophysical activity beneath the skin surface associated with tumor growth results in a higher metabolic rate which, in turn, results in an elevated temperature in that tissue. This appears as a hotspot in a thermal image containing that tissue. Recently, interest has been rekindled in thermography as a breast cancer screening approach with the improvement in thermal camera resolution and technology. Radiologists and thermographers are increasingly demanding more powerful software interface tools to assist them.

Accordingly, what is needed in this art are increasingly sophisticated software tools which enable medical practitioners to manually or automatically analyze a thermal image of an area of breast tissue for the presence of tumorous tissue.

BRIEF SUMMARY

What is disclosed is a software tool which enables medical practitioners to manually or automatically analyze a thermal image of an area of breast tissue for the presence of tumorous tissue. In one embodiment, the software interface tool disclosed herein comprises a user-selectable patient details object which enables the display of a patient details screen wherein a user can enter, edit, view, save and retrieve patient information. A selectable thermal analysis object which enables a user to analyze a displayed thermal image of a breast of a patient for breast cancer screening and to classify tissue identified in the thermal image as being tumorous. A modalities object concludes the patient evaluation, persists all data collected from other sections of the tool, and generates reports for documentation purposes. All this data is then stored in a database that contains records of all breast cancer screening patients. The information can be captured from the database and edited and analyzed further using the tool. Also, report containing all the relevant data is generated for doctor's reference.

Features and advantages of the above-described software interface will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

Figure 1:
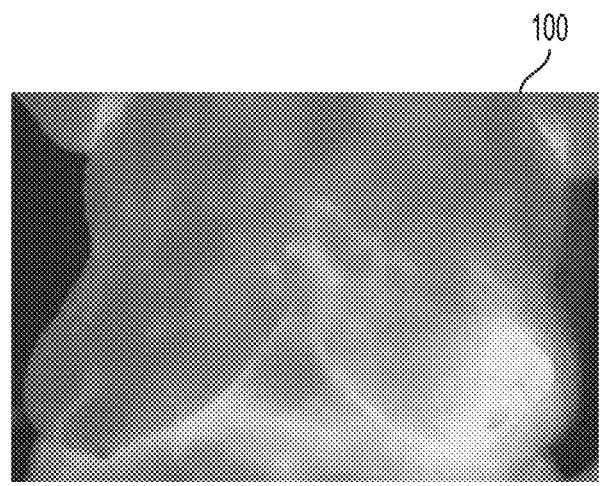
FIG. 1 shows an example thermal image of the breast of a female patient.

What is disclosed is a software tool which enables medical practitioners to manually or automatically analyze a thermal image of an area of breast tissue for the presence of tumorous tissue.

Non-Limiting Definitions

A "person" refers to either a male or a female. Gender pronouns are not to be viewed as limiting the scope of the appended claims strictly to females. Moreover, although the term "person" or "patient" is used interchangeably throughout this disclosure, it should be appreciated that the person undergoing breast cancer screening may be something other than a human such as, for example, a primate. Therefore, the use of such terms is not to be viewed as limiting the scope of the appended claims to humans.

A "thermal imaging system" is a camera with a lens that focuses infrared energy from objects in a scene onto an array of specialized sensors which convert infrared energy into electrical signals on a per-pixel basis and outputs a thermal image comprising an array of pixels with color values corresponding to surface temperatures of the objects in the image across a thermal wavelength band. The thermal imaging system can be any of: a single-band infrared camera, a multi-band infrared camera in the thermal range, and a hyperspectral infrared camera in the thermal range. Specialized processors inside the thermal camera associate pixel color values with different temperatures and provide output color values of each pixel in the resulting thermal image. The resolution for a thermal camera is effectively the size of the pixel. Smaller pixels mean that more pixels will go into the image for the same region of interest giving the resulting image higher resolution and thus better spatial definition. Because the amount of black-body radiation emitted by an object increases with the object's temperature, variations in temperatures of objects are observable in a thermal image. Thermal cameras generally consist of five primary components: 1) optics comprising specialized focal plane arrays (FPAs) that respond to defined wavelengths of the infrared range of the electromagnetic (EM) spectrum ($\approx 7.5$ to $\approx 14$ μm); 2) a detector for detecting radiation in the infrared range; 3) an amplifier for amplifying the received radiation; 4) a display for viewing the captured images; and 5) signal processing hardware such as: a CPU, memory, storage, for performing mathematical algorithms which interpret data and construct an IR image. Common thermal imaging systems include: InSb, InGaAs, HgCdTe, and QWIP FPA. Newer technologies utilize an uncooled Microbolometer as FPA sensors. Thermal cameras offer a relatively large dynamic range of temperature settings. However, for the purposes hereof, it is preferable that the camera's temperature range be relatively small centered around subject's body surface temperature so that small temperature variations are amplified in terms of pixel color changes to provide a better measure of temperature variation. Thermal cameras are readily available in various streams of commerce. Thermal images are captured using a thermal imaging system.

A "thermal image" comprises a plurality of pixels with each pixel having an associated corresponding temperature value. Pixels in the thermal image with a higher temperature value being displayed in a first color and pixels with a lower temperature value are displayed in a second color. Pixels with temperature values between the lower and higher temperature values are displayed in gradations of color between the first and second colors. FIG. 1 show a thermal camera 100 of a patient's breasts. The thermal images are received by the workstation for manipulation by various aspects of the functionality of the software interface disclosed herein. Although the thermal images herein are shown in black/white, it should be appreciated that thermal images are in color. Thermal images can be retrieved from a memory or storage device of the thermal imaging device, or obtained from a remote device over a network. Thermal images may be retrieved from a media such as a CDROM or DVD. Thermal images may be downloaded from a web-based system which makes such images available for processing. Thermal images can also be retrieved using an application such as those which are widely available for handheld cellular devices and processed on the user's cellphone or other handheld computing device such as an iPad or tablet. Thermal images are of a breast area of a patient which encompasses tissue of the breast itself and may further include portions of surrounding non-breast tissue. Regions of breast tissue are automatically or manually identified in the thermal image for analysis.

Figure 2:
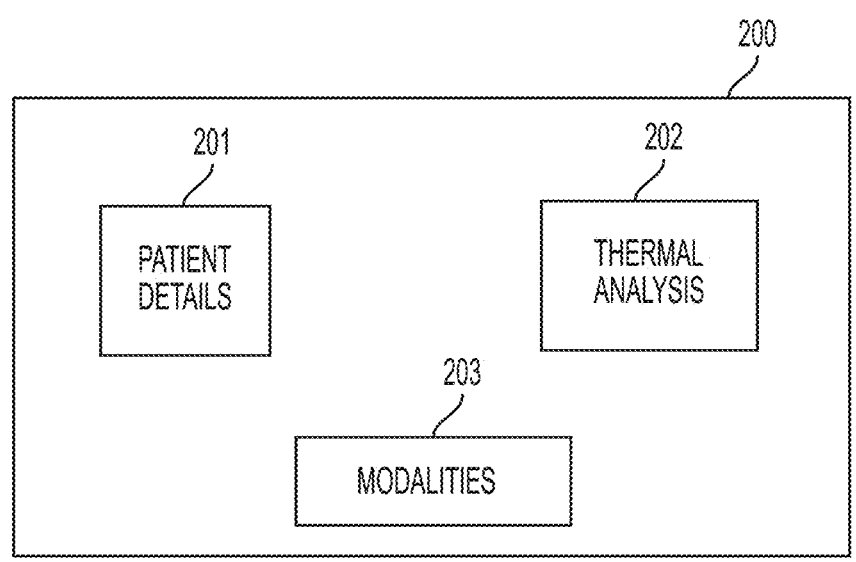
FIG. 2 shows one embodiment of the present software interface tool.

A "software interface tool" is a composite of user-selectable functionality displayed on a display device such as a touchscreen display of a computer workstation. FIG. 2 shows one example embodiment of the present software interface tool 200. The breast cancer screening tool allows a user to analyze thermal images for semi-automatic detection and classification of breast tumors. The tool consists of three sections: 1) patient data acquisition, 2) thermal data analysis, and 3) modalities, conclusion, data storage, and report generation. Various embodiments of the present software interface tool comprise a plurality of user-selectable functional objects.

A "user-selectable function object" is a graphical widget which can take a variety of forms such as, for instance, a button, or the like, as are commonly known in the software arts. Machine executable program instructions associated with a particular "object" performs certain functionality when selected by a user clicking, for instance, a mouse thereon or manually touching a touch-sensitive display screen.

A "PATIENT DETAILS" object 201 enables the display of a screen where a user can enter, edit, view, store and retrieve patient information such as, for example, name, age, date, medical history, examination details, patient complaints, and the like. This section of the software tool captures relevant information needed as a pre-requisite for patient classification and conclusion. The section allows the user to enter patient demographic information, patient cancer history, family cancer history, patient medical history, patient complaints, and clinical examination. The information captured in this section helps to compute the probability of a patient developing breast cancer. For example, history of cancer present in patient and/or her family increases the chances of developing cancer in the future. Patient medical history plays an important role in final diagnosis of the patient for example medical history like pregnant or lactating mothers suggests that it might lead to temperature increase seen in the thermal images. Moreover, medical history of patient gives insight into any benign conditions that may lead to cancer. Patient complaints and clinical/physical examination give relevant information on the present condition of the patient, which include important data on hormonal levels, breast nodules, and other factors. The entire patient information acquisition screen captures data to help evaluate the patient's condition in a holistic manner.

Figure 3:
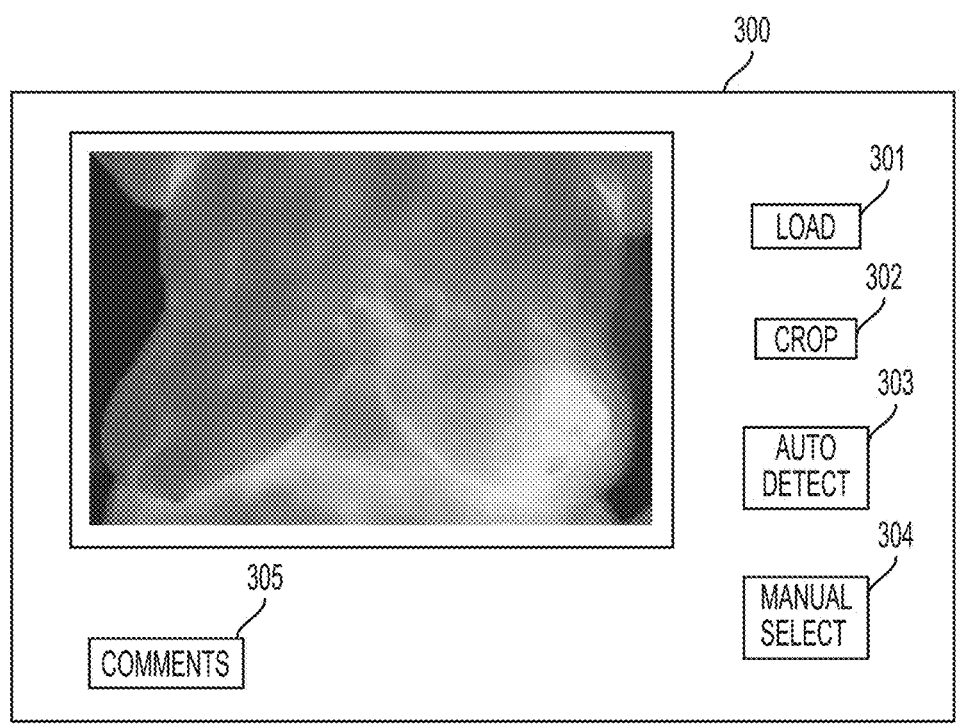
FIG. 3 shows one embodiment of the present software interface tool wherein the thermal image of FIG. 1 is displayed for breast cancer screening.

A "THERMAL ANALYSIS" object 202 enables the display of a screen where a user/radiologist can analyze a thermal image of a breast of a patient for breast cancer screening. The thermal analysis in the software interface tool classifies the patient as normal, benign, malignant, or bilateral. One embodiment of the displayed thermal analysis screen is shown in FIG. 3. For example, the object 303 in the FIG. 3 may trigger the automatic analysis and classification of the thermal image.

A "MODALITIES" object 203 enables the display of a image screen where a user/radiologist can enter, edit, view, store and retrieve patient information from other tests such as, for example, patient surgeries, mammography details, sonomammography findings, x-rays, biopsies, pathology reports, physician notes, and the like. This section of the tool concludes the patient evaluation, persists all data collected from other sections of the tool, and generates reports for documentation purposes. All this data is then stored in a database that contains records of all breast cancer screening patients. The information can be captured from the database and edited and analyzed further using the tool. Also, report containing all the relevant data is generated for doctor's reference.

Thermal Analysis Screen

Thermographic data can be obtained using, for instance, a Meditherm camera, with a resolution of 690×478 pixels. There is a specific protocol for capturing the thermography images of the subject. The subject is asked to wear a loose fitting gown and wait in an AC room for 15 minutes so that there is normalization of body temperature and external heat conditions are minimized. The subject is then seated on a swivel chair at a fixed distance from the thermography camera. The camera focus is zoomed in so that only the relevant region of the subject's body is captured; from below the neck to just below the infra-mammary fold. The subject's chair is also swiveled to capture the thermal image of the subject at different angles to cover entire breast. In one embodiment, the angle of capture is frontal, at 45° oblique, i.e. right and left oblique, and right/left lateral. The thermography camera temperature range is also calibrated within 8° C. range for each subject, with the maximum temperature of this range corresponding to the maximum body temperature of the person. This would allow the maximum body temperature of the person to be observed at the color corresponding to the image's maximum temperature (in this case white). This is to assist in visual interpretation of the image by the radiologist/thermographer. The default view of the thermal analysis screen shows the isotherm view, where pixels within every 0.5° C. range are in a different color. The thermographers/radiologists find this isotherm view helpful and typically make most of their observations based on this view.

Thermal patterns identified in one or both of the right and left breast are used to determine the presence/absence of cancer or any abnormality. The infra-mammary folds are hot normally due to friction, and hence are not considered. The lymph nodes in the axilla regions are also possible regions where there may be metastasis of breast cancer and are typically examined in sonomammograms. In thermograms, the axilla regions are generally hot due to friction and the presence of lymph nodes. In one embodiment, six thermal images are typically captured for each cancer subject. Once the thermal images have been captured by the camera, they are uploaded into the thermal analysis screen. One embodiment of the screen 300 displayed when the user selects the object 202 of FIG. 2 enables the following user-selectable functional objects.

A "LOAD" object 301 enables a user to upload a thermal image of the patient captured in different views.

A "CROP" object 302 enables a user to crop a block of pixels from the displayed thermal image for tumor classification.

An "AUTO-DETECT" object 303 which enables the user to initiate a tumor auto-detection algorithm. If any suspected tumor detected, the algorithm highlights the tumor region, displays it in the best possible view and displays a message saying "suspected malignancy detected". If no suspected tumor is detected, then it just displays the frontal view thermal image with a message "no tumor present". The tool provides the user the facility to confirm whether the output of auto-detect algorithm is correct or not. This is important to improve the accuracy of the auto-detect tumor algorithm.

A "MANUAL SELECT" object 304 which enables a user to choose a desired cropped region to be displayed in either a 2D or 3D contour view and further allows the user to mark the suspected tumor regions. This allows the best possible thermal image view along with the highlighted suspected tumor region to be displayed. The user perform the manual-select process only when the user suspects any tumor is present.

A "COMMENTS" object 305 which enables the user to enter the thermo-biological score of the patient and quadrant-wise comments for right breast and left breast with respect to the captured thermal images along with any other medically relevant comments deemed necessary.

Tumor Classification Method

Cancerous tumors are typically "hot", and are significantly hotter than the surrounding tissue. Small tumors in the earlier stages of cancer growth are "warm." As the surface body temperature is observed to vary by a few degree centigrade across subjects, the temperature thresholds to determine "hot" areas need to be subject dependent, and based on the temperature distribution over a given block of pixels in the thermal image. Weak edges in the temperature map can also be obtained around the tumors, but may not have closed boundaries. Temperature thresholds based on the temperature distribution and edges around the tumor may be used to detect the tumor region. The following rules are used to classify a particular block of pixels in the thermal image. Rule 1: ($R_1$) If k1% of a block of pixels in tissue identified in the thermal image have a temperature above a threshold $\theta_1$ which is computed based on temperature distribution, classify the identified tissue as tumorous. Rule 2: ($R_2$) If $k_2$% of a block of pixels in the thermal image have a temperature above a threshold ($T_{max}-\theta_2$), where $\theta_2$ is a constant value computed from the thermal image and $T_{max}$ is the maximum body temperature, then classify the identified tissue as tumorous. Rule 3: ($R_3$) If $k_3$% of a block of pixels in the thermal image have a temperature below a threshold $\theta_3$ computed based on distribution body surface temperature then classify the identified tissue as normal. Rule 4: ($R_4$) if the edge length of a block of pixels is $k_4$% of the perimeter of the block then classify the tissue as tumorous. The $k_1$, $k_2$, $k_3$, and $k_4$ are computed by the second processor using the thermal image. These block decisions are combined using a decision rule to maximize tumor detection & classification and minimize false positives. In one embodiment, the decision rule is a majority rule of ($R_1$, $R_2$, $R_3$, $R_4$). In another embodiment, the decision rule is a weighted sum of ($R_1$, $R_2$, $R_3$, $R_4$) where the weights are based on an inter-dependence of these features in tumor detection and medical experience.

This algorithm can be tuned based on experience to maximize tumor detection and classification in subjects. Additional stages of classification can be employed to re-classify subjects. Further, screening could be improved with better imaging protocols, such as cooling the subject to remove heat generated by external causes. Specificity can be improved with additional algorithms that determine high risk subjects with excessive hormonal responses and that separate borderline suspicious cases into different categories.

The present breast cancer screening tool can also be modified in future to take into account the age and medical history along with thermography data to improve sensitivity and specificity. The imaging protocols can be modified or additional questions to the subject can be asked to rule out external heat conditions. If the heat persists after this additional cooling protocol, then it would be due to malignancy, inflammation or infection. Questions could include whether the subject was exposed to some external conditions causing heat generation.

Example Networked Environment

Figure 4:
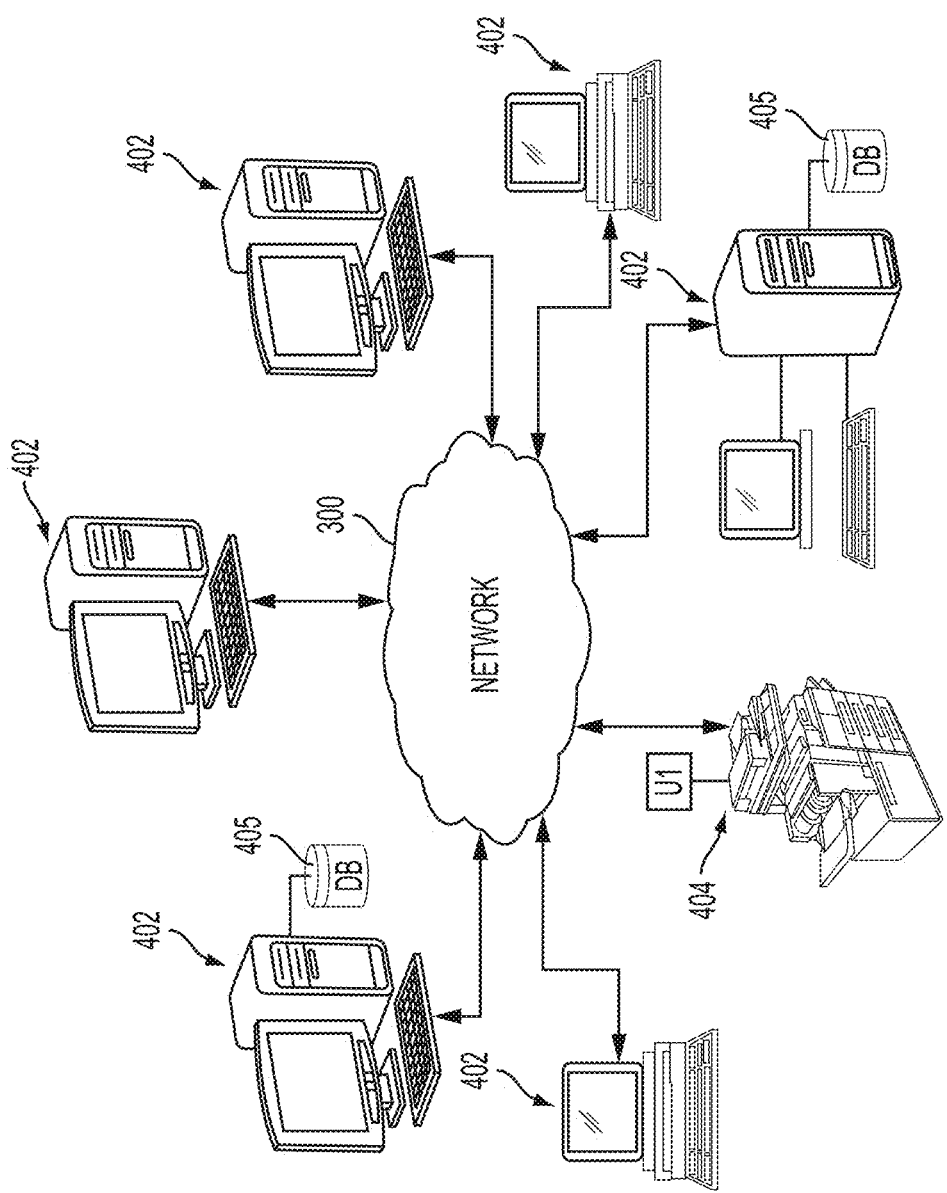
FIG. 4 illustrates one example of a networked computing environment wherein various features of the present software interface tool for breast cancer screening can be implemented.

Reference is now being made to FIG. 4 which is one example of a networked computing environment wherein various features of the present software interface tool for breast cancer screening will find its intended uses. The following is intended to provide a general description of a suitable networked computing environment where various medical practitioners are simultaneously performing breast cancer screening using the present software interface tool. It should be understood that other computing environments are equally capable of providing various features hereof.

In FIG. 4, a computing environment places a plurality of computer system 402 and 406, (collectively referred to as computing devices) in communication with each other over a network 400 such as internet. The networked environment also includes a document reproduction device 404 capable of printing patient results and reports. Each of the networked computing devices generally includes a mouse, keyboard, and a display such as a CRT, LCD, touchscreen display, or the like. Each of the computing devices also includes a processor capable of executing machine readable program instructions. The processor is in digital communication with a main memory for storing data which may include RAM, DRAM, and the like. The computing devices each further includes a hard drive and a removable storage unit capable of reading/writing to a storage media such as a floppy disk, magnetic tape, optical disk, CD-ROM, DVD, etc. Each of the computing devices further includes an internal network interface capable of sending information through a routing device (not shown) to internet 400. The computing device may include an Ethernet card or similar network interface card to connect to the Internet using, for example, a cable modem. Typical network interfaces include special purpose systems such as a local area network (LAN) or wireless area network (WAN). Those of ordinary skill will readily appreciate that a networked computing environment capable of transmitting and receiving patient records can occur on a variety of networked environments other than the environment of FIG. 4.

Many aspects of the internet 400, illustrated as an amorphous cloud, are commonly known. As such, a detailed discussion as to the operation of the internet has been omitted. Suffice it to say, data packets are transmitted by a network of special purpose servers connected via a plurality of communication links. Data is transferred in the form of signals which may be, for example, electrical, electronic, electro-magnetic, optical, or other signals. These signals are transmitted by wire, cable, fiber optic, phone line, cellular link, RF, satellite, or any other medium or communications link known in the arts. One computing device with access to the internet communicates with another computing device with access to the internet using well established communication protocols.

In the networked environment of FIG. 4, computer system 406 also includes database 405 capable of storing and retrieving patient records in response to a query. The database is also capable of adding new data records, updating stored records, and displaying stored data and other information made available by the database engine. Since database construction, query optimization, indexing methods, and record retrieval techniques and algorithms are well known in the arts, a further discussion as to a specific database implementation is omitted. One of ordinary skill would be able to obtain a database engine known in the arts and place the database in communication with any of the computing devices and the printing system. It should be appreciated that the database provided herewith for the storing and retrieving information using any of the networked devices shown. The implementation of the database with computer 406 is but one configuration. Whichever networked device the database is associated with on internet, it should be understood that information can be sent to any device connected to the network 400.

The teachings hereof can be implemented in hardware or software using any known or later developed systems, structures, devices, and/or software by those skilled in the applicable art without undue experimentation from the functional description provided herein with a general knowledge of the relevant arts. Moreover, the methods hereof can be implemented as a routine embedded on a personal computer or as a resource residing on a server or workstation, such as a routine embedded in a plug-in, a driver, or the like. The teachings hereof may be partially or fully implemented in software using object or object-oriented software development environments that provide portable source code that can be used on a variety of computer, workstation, server, network, or other hardware platforms. One or more of the capabilities hereof can be emulated in a virtual environment as provided by an operating system and other specialized programs such Windows or Java.

One or more aspects of the teaching disclosed herein are intended to be incorporated in an article of manufacture, including one or more computer program products, having computer usable or machine readable media. The article of manufacture may be included on at least one storage device readable by a machine architecture embodying executable program instructions capable of performing the methods described herein. The article of manufacture may be shipped, sold, leased, or otherwise provided separately either alone or as part of an add-on, update, upgrade, or product suite.

It will be appreciated that the above-disclosed and other features and functionality, or alternatives thereof, may be desirably combined into many other different systems or applications. As such, various presently unforeseen or unanticipated alternatives, modifications, variations, or improvements therein may become apparent and/or subsequently made by those skilled in the art which are also intended to be encompassed by the following claims. Accordingly, the embodiments set forth above are illustrative and not limiting. Changes to the above-described embodiments may be made without departing from the spirit and scope of the invention.

The teachings of any printed publications including patents and patent applications, are each separately hereby incorporated by reference in their entirety.

What is claimed is:

1. A system for processing a thermal image, the system comprising:
a computing device comprising:
a memory that stores a thermal image and a set of instructions; and
a processor that executes the set of instructions for processing the thermal image by performing the steps of:
receiving the thermal image of a patient's breast, wherein the thermal image is captured by a thermal imaging camera, the thermal imaging camera comprising:
an array of sensors that converts infrared energy into electrical signals on a per-pixel basis;
a lens that focuses the infrared energy from the patient's breast onto the array of sensors, wherein the array of sensors detects temperature values from the patient's breast; and
a specialized processor that processes the detected temperature values into at least one block of pixels to generate the thermal image;
uploading the thermal image of the patient's breast captured in different views onto the computing device;
comparing the temperature values of the at least one block of pixels in the thermal image with temperature thresholds, wherein the temperature thresholds comprises a threshold $\theta 1$, a threshold $(T_{max}-\theta 2)$, and a threshold $\theta 3$, wherein values of the threshold $\theta 1$, the threshold $(T_{max}-\theta 2)$, and the threshold $\theta 3$ are obtained based on a temperature distribution in the patient's breast;
computing multiple percentage values (k1, k2, k3, k4) of the at least one block of pixels in the thermal image with a temperature satisfying the compared temperature thresholds;
determining whether an edge length of a block of pixels is $k_4$% of a perimeter of the block;
processing a decision rule R to determine pixels in the thermal image that indicate a malignant tumor based on the percentage values (k1, k2, k3, k4); and
displaying a boundary of a block of pixels in the thermal image indicating the malignant tumor in a first color and displaying a boundary of a block of pixels in the thermal image indicating a non-malignant tumor in a second color.

2. The system of claim 1, wherein the decision rule R determines whether a pixel is tumorous or not based on a weighted sum of decision rules $(R_1, R_2, R_3, R_4)$.

3. The system of claim 1, wherein the method of detecting the tumorous region in the thermal image comprises normalizing a body temperature of the patient to minimize external heat condition before taking the thermal image.

4. A non-transitory computer-readable storage medium that stores a thermal image capture from a thermal imaging camera and set of instructions for processing the thermal image by performing the steps of:
receiving the thermal image of a patient's breast, wherein the thermal image is captured by a thermal imaging camera, the thermal imaging camera comprising:
an array of sensors that converts infrared energy into electrical signals on a per-pixel basis;
a lens that focuses the infrared energy from the patient's breast onto the array of sensors, wherein the array of sensors detects temperature values from the patient's breast; and
a specialized processor that processes the detected temperature values into at least one block of pixels to generate the thermal image;
uploading the thermal image of the patient's breast captured in different views onto the computing device;
comparing temperature values of at least one block of pixels in the thermal image with temperature thresholds, wherein the temperature thresholds comprises a threshold $\theta_1$, a threshold $(T_{max}-\theta_2)$, and a threshold $\theta_3$, wherein values of the threshold $\theta_1$, the threshold $(T_{max}-\theta_2)$, and the threshold $\theta_3$ are obtained from temperature distribution in a patient's breast;
computing multiple percentage values (k1, k2, k3, k4) of the at least one block of pixels in the thermal image with a temperature satisfying the compared temperature thresholds;
determining whether an edge length of a block of pixels is $k_4$% of a perimeter of the block;
processing a decision rule R to determine pixels in the thermal image that indicate a malignant tumor based on the percentage values (k1, k2, k3, k4); and
displaying a boundary of a block of pixels in the thermal image indicating the malignant tumor in a first color and displaying a boundary of a block of pixels in the thermal image indicating a non-malignant tumor in a second color.

5. The non-transitory computer-readable storage medium of claim 4, wherein the method comprises identifying a block of pixels from the thermal image using a tissue segmentation object.

6. The non-transitory computer-readable storage medium of claim 4, wherein the method of detecting tumorous region in the thermal image comprising:
identifying a suspected tumor region by highlighting the suspected tumor region using an auto-detection; and
identifying the suspected tumor region by selecting the suspected tumor region using a manual select object.

7. The non-transitory computer-readable storage medium of claim 4, wherein the method comprises providing a statistical analysis object for performing a statistical analysis with respect to any of: patient information, tumor detection, diagnosis, demographics and thermal images.

8. The non-transitory computer-readable storage medium of claim 4, wherein the method comprises providing a modalities object which enables a user to enter, edit, view, save and retrieve a patient data comprising any of: surgeries, mammography details, sonomammography findings, x-rays, biopsies, pathology reports, physician notes, and images.

9. The non-transitory computer-readable storage medium of claim 4, wherein a dynamic representation of data inputs are shown depending on an entry of the inputs.

10. The non-transitory computer-readable storage medium of claim 4, wherein the patient data including data modalities are dynamically and automatically parsed and retrieved through an information architecture and displayed to the user.

11. The non-transitory computer-readable storage medium of claim 4, wherein the method comprises providing a transmit object which enables the user to upload any patient data to a remote device.

12. The non-transitory computer-readable storage medium of claim 4, wherein the method comprises providing a thermal camera object which enables the user to manipulate and configure the thermal camera acquiring the thermal images or video.

13. The non-transitory computer-readable storage medium of claim 4, wherein the method comprising providing an orientation object which enables the user to change a view angle of the breast in the thermal image.

14. The non-transitory computer-readable storage medium of claim 4, wherein the thermal image is pre-processed using image processing techniques to obtain a visualization suitable for further examination by a user.

15. The non-transitory computer-readable storage medium of claim 4, wherein the method comprises providing an isotherm object which enables the user to display 2D and 3D contour lines on the thermal image at a desired resolution, the contour lines bounding pixels in the thermal image having substantially similar temperature values.

16. The non-transitory computer-readable storage medium of claim 4, wherein the method comprises providing a view angle object which automatically determines a view angle of the breast in the thermal image views using the body contours and shape.

17. The non-transitory computer-readable storage medium of claim 4, wherein the method comprises providing a comments object which enables the user to enter the thermo-biological score of the patient and quadrant-wise comments for right breast and left breast with respect to the captured thermal images along with any other medically relevant comments deemed necessary.

18. The non-transitory computer-readable storage medium of claim 4, wherein a software interface for breast cancer screening is implemented in a networked architecture comprising a plurality of computer workstations.

19. The non-transitory computer-readable storage medium of claim 18, wherein the networked architecture further comprises a cloud-based storage and processing.

* * * * *